United States Patent [19]
Stashenko et al.

[11] Patent Number: 5,656,728
[45] Date of Patent: Aug. 12, 1997

[54] HUMAN OSTOCLAST-SPECIFIC AND -RELATED GENES

[75] Inventors: Philip Stashenko, Norfolk; Yi-Ping Li, Boston; Anne L. Wucherpfennig, Brookline, all of Mass.

[73] Assignee: Forsyth Dental Infirmary for Children, Boston, Mass.

[21] Appl. No.: 456,701

[22] Filed: Jun. 1, 1995

Related U.S. Application Data

[62] Division of Ser. No. 392,678, Feb. 23, 1995, Pat. No. 5,552,281, which is a continuation of Ser. No. 45,270, Apr. 6, 1993, abandoned.

[51] Int. Cl.[6] .............................. C07K 5/00; C07K 14/00; C07K 14/51; C07H 21/04
[52] U.S. Cl. ........................ 530/350; 530/300; 530/324; 530/325; 530/326; 530/327; 530/356; 536/23.1; 536/23.2
[58] Field of Search ...................... 530/350, 356, 530/300, 324, 325, 326, 327; 536/23.1, 23.2

[56] References Cited

U.S. PATENT DOCUMENTS 5,501,969  3/1996  Hastings et al. ................. 435/240.2

OTHER PUBLICATIONS

Blair, Harry C., et al., "Extracellular-matrix degradation at acid ph Avian osteoclast acid collagenase isolation and characterization," *Biochemical Journal* 290 (3):873–884 (15 Mar. 1993).

Tezuka, Ken–Ichi, et al., "Identification of osteopontin in isolated rabbit osteoclasts," *Biochemical and Biophysical Research Communications* 186 (2):911–917 (31 Jul. 1992).

Tezuka, Ken–Ichi, et al., "Molecular cloning of a possible cysteine proteinase predominantly expressed in osteoclasts'," *Journal of Biological Chemistry*, 269(2) :1106–1109, (14 Jan. 1994).

Horton, M.A. et al., "Monoclonal Antibodies to Osteoclastomas (Giant Cell Bone Tumors): Definition ot Osteoclast-specific cellular Antigens," *Cancer Research*, 45:5663–5669 (Nov. 1985).

Davies, J. et al., "The Osteoclast Functional Antigen, Implicated in the Regulation of Bone Resoption, Is Biochemically Related to the Vitronectin Receptor," *The J. of Cell Biology*, 109:1817–1826 (Oct. 1989).

Hayman, A.R. et al., "Purification and Characterization of a Tartrate–resistant Acid Phosphatase from Human Osteoclastomas," *Biochem. J.*, 261:601–609 (1989).

Sandberg, M. et al., "Localization of the Expression of Types I, III, and IV Collagen, TGF-$\beta$1 and c-fos Genes in Developing Human Calvarial Bones," *Developmental Biology*, 130:324–334 (1988).

Sandberg, M. et al., "Enhanced Expression of the TGF-$\beta$ and c–fos mRNAs in the growth Plates of Developing Human Long Bones," *Development*, 102:461–470 (1988).

Ek–Rylander, B. et al., "Cloning, Sequence, and Developmental Expression of a Type 5, Tartrate–Resistant, Acid Phosphatase of Rat Bone," *The J. of Biological Chem.*, 266:24684–24689 (Dec. 25, 1991).

Schwabe, G., Database Genbank, Locus HSRPRNA (1 Page) Dec. 4, 1991.

Marzuki, S., Database Genbank, Locus MIHSGENOM (3 Pages) Aug. 27, 1992.

Primary Examiner—W. Gary Jones
Assistant Examiner—Paul B. Tran
Attorney, Agent, or Firm—Hamilton, Brook, Smith & Reynolds, P.C.

[57] ABSTRACT

The present invention relates to purified DNA sequences encoding all or a portion of an osteoclast-specific or -related gene products and a method for identifying such sequences. The invention also relates to antibodies directed against an osteoclast-specific or -related gene product. Also claimed are DNA constructs capable of replicating DNA encoding all or a portion of an osteoclast-specific or -related gene product, and DNA constructs capable of directing expression in a host cell of an osteoclast-specific or -related gene product.

3 Claims, 1 Drawing Sheet

```
1     AGACACCTCT GCCCTCACCA TGAGCCTCTG GCAGCCCCTG GTCCTGGTGC TCCTGGTGCT
61    GGGCTGCTGC TTTGCTGCCC CCAGACAGCG CCAGTCCACC CTTGTGCTCT TCCCTGGAGA
121   CCTGAGAACC AATCTCACCG ACAGGCAGCT GGCAGAGGAA TACCTGTACC GCTATGGTTA
181   CACTCGGGTG GCAGAGATGC GTGGAGAGTC GAAATCTCTG GGGCCTGCGC TGCTGCTTCT
241   CCAGAAGCAA CTGTCCCTGC CCGAGACCGG TGAGCTGGAT AGCGCCACGC TGAAGGCCAT
301   GCGAACCCCA CGGTGCGGGG TCCCAGACCT GGGCAGATTC CAAACCTTTG AGGGCGACCT
361   CAAGTGGCAC CACCACAACA TCACCTATTG GATCCAAAAC TACTCGGAAG ACTTGCCGCG
421   GGCGGTGATT GACGACGCCT TTGCCCGCGC CTTCGCACTG TGGAGCGCGG TGACGCCGCT
481   CACCTTCACT CGCGTGTACA GCCGGGACGC AGACATCGTC ATCCAGTTTG GTGTCGCGGA
541   GCACGAGAC GGGTATCCCT TCGACGGGAA GGACGGGCTC CTGCACACG CCTTTCCTCC
601   TGGCCCCGGC ATTCAGGGAG ACGCCCATTT CGACGATGAC GAGTTGTGGT CCCTGGGCAA
661   GGGCGTCGTG GTTCCAACTC GGTTTGGAAA CGCAGATGGC GCGGCCTGCC ACTTCCCCTT
721   CATCTTCGAG GGCCGCTCCT ACTCTGCCTG CACCACCGAC GGTCGCTCCG ACGGGTTGCC
781   CTGGTGCAGT ACCACGGCCA ACTACGACAC CGACGACCGG TTTGGCTTCT GCCCCAGCGA
841   GAGACTCTAC ACCCGGGACG GCAATGCTGA TGGGAAACCC TGCCAGTTTC CATTCATCTT
901   CCAAGGCCAA TCCTACTCCG CCTGCACCAC GGACGGTCGC TCCGACGGCT ACCGCTGGTG
961   CGCCACCACC GCCAACTACG ACCGGGACAA GCTCTTCGGC TTCTGCCCGA CCCGAGCTGA
1021  CTCGACGGTG ATGGGGGGCA ACTCGGCGGG GGAGCTGTGC GTCTTCCCCT TCACTTTCCT
1081  GGGTAAGGAG TACTCGACCT GTACCAGCGA GGGCCGCGGA GATGGGCGCC TCTGGTGCGC
1141  TACCACCTCG AACTTTGACA GCGACAAGAA GTGGGGCTTC TGCCCGGACC AAGGATACAG
1201  TTTGTTCCTC GTGGCGGCGC ATGAGTTCGG CCACGCGCTG GCTTAGATC ATTCCTCAGT
1261  GCCGGAGGCG CTCATGTACC CTATGTACCG CTTCACTGAG GGGCCCCCT TGCATAAGGA
1321  CGACGTGAAT GGCATCCGGC ACCTCTATGG TCCTCGCCCT GAACCTGAGC CACGGCCTCC
1381  AACCACCACC ACACCGCAGC CCACGGCTCC CCCGACGGTC TGCCCCACCG GACCCCCCAC
1441  TGTCCACCCC TCAGAGCGCC CCACAGCTGG CCCCACAGGT CCCCCCTCAG CTGGCCCCAC
1501  AGGTCCCCCC ACTGCTGGCC CTTCTACGGC CACTACTGTG CCTTTGAGTC CGGTGGACGA
1561  TGCCTGCAAC GTGAACATCT TCGACGCCAT CGCGGAGATT GGGAACCAGC TGTATTTGTT
1621  CAAGGATGGG AAGTACTGGC GATTCTCTGA GGGCAGGGGG AGCCGGCCGC AGGGCCCCTT
1681  CCTTATCGCC GACAAGTGGC CCGCGCTGCC CCGCAAGCTG GACTCGGTCT TTGAGGAGCC
1741  GCTCTCCAAG AAGCTTTTCT TCTTCTCTGG GCGCCAGGTG TGGGTGTACA CAGGCGCGTC
1801  GGTGCTGGGC CCGAGGCGTC TGGACAAGCT GGGCCTGGGA GCCGACGTGG CCCAGGTGAC
1861  CGGGGCCCTC CGGAGTGGCA GGGGAAGAT GCTGCTGTTC AGCGGGCGGC GCCTCTGGAG
1921  GTTCGACGTG AAGGCGCAGA TGGTGGATCC CCGGAGCGCC AGCGAGGTGG ACCGGATGTT
1981  CCCCGGGGTG CCTTTGGACA CGCACGACGT CTTCCAGTAC GAGAGAAAG CCTATTTCTG
2041  CCAGGACCGC TTCTACTGGC GCGTGAGTTC CCGGAGTGAG TTGAACCAGG TGGACCAAGT
2101  GGGCTACGTG ACCTATGACA TCCTGCAGTG CCCTGAGGAC TAGGGCTCCC GTCCTGCTTT
2161  GCAGTGCCAT GTAAATCCCC ACTGGGACCA ACCCTGGGGA AGGAGCCAGT TTGCCGGATA
2221  CAAACTGGTA TTCTGTTCTG GAGGAAAGGG AGGAGTGGAG GTGGGCTGGG CCCTCTCTTC
2281  TCACCTTTGT TTTTTGTTGG AGTGTTTCTA ATAAACTTGG ATTCTCTAAC CTTT
```

Figure 1

HUMAN OSTOCLAST-SPECIFIC AND -RELATED GENES

RELATED APPLICATIONS

This application is a divisional application of pending U.S. application Ser. No. 08/392,678, filed Feb. 23, 1995 now U.S. Pat. No. 5,552,281, which is a file wrapper continuation of U.S. application Ser. No. 08/045,270, filed Apr. 6, 1993 (abandoned). The teachings of these prior applications are incorporated herein by reference in their entirety.

BACKGROUND OF THE INVENTION

Excessive bone resorption by osteoclasts contributes to the pathology of many human diseases including arthritis, osteoporosis, periodontitis, and hypercalcemia of malignancy. During resorption, osteoclasts remove both the mineral and organic components of bone (Blair, H. C., et al., *J. Cell Biol.* 102:1164 (1986)). The mineral phase is solubilized by acidification of the sub-osteoclastic lacuna, thus allowing dissolution of hydroxyapatite (Vaes, G., *Clin. Orthop. Relat.* 231:239 (1988)). However, the mechanism(s) by which type I collagen, the major structural protein of bone, is degraded remains controversial. In addition, the regulation of osteoclastic activity is only partly understood. The lack of information concerning osteoclast function is due in part to the fact that these cells are extremely difficult to isolate as pure populations in large numbers. Furthermore, there are no osteoclastic cell lines available. An approach to studying osteoclast function that permits the identification of heretofore unknown osteoclast-specific or -related genes and gene products would allow identification of genes and gene products that are involved in the resorption of bone and in the regulation of osteoclastic activity. Therefore, identification of osteclast-specific or -related genes or gene products would prove useful in developing therapeutic strategies for the treatment of disorders involving aberrant bone resorption.

SUMMARY OF THE INVENTION

The present invention relates to isolated DNA sequences encoding all or a portion of osteoclast-specific or -related gene products. The present invention further relates to DNA constructs capable of replicating DNA encoding osteoclast-specific or -related gene products. In another embodiment, the invention relates to a DNA construct capable of directing expression of all or a portion of the osteoclast-specific or -related gene product in a host cell.

Also encompassed by the present invention are prokaryotic or eukaryotic cells transformed or transfected with a DNA construct encoding all or a portion of an osteoclast-specific or -related gene product. According to a particular embodiment, these cells are capable of replicating the DNA construct comprising the DNA encoding the osteoclast-specific or -related gene product, and, optionally, are capable of expressing the osteoclast-specific or -related gene product. Also claimed are antibodies raised against osteoclast-specific or -related gene products, or portions of these gene products.

The present invention further embraces a method of identifying osteoclast-specific or -related DNA sequences and DNA sequences identified in this manner. In one embodiment, cDNA encoding osteoclast is identified as follows: First, human giant cell tumor of the bone was used to 1) construct a cDNA library; 2) produce $^{32}$P-labelled cDNA to use as a stromal cell$^+$, osteoclast$^+$ probe, and 3) produce (by culturing) a stromal cell population lacking osteoclasts. The presence of osteoclasts in the giant cell tumor was confirmed by histological staining for the osteoclast marker, type 5 tartrate-resistant acid phosphatase (TRAP) and with the use of monoclonal antibody reagents.

The stromal cell population lacking osteoclasts was produced by dissociating cells of a giant cell tumor, then growing and passaging the cells in tissue culture until the cell population was homogeneous and appeared fibroblastic. The cultured stromal cell population did not contain osteoclasts. The cultured stromal cells were then used to produce a stromal cell$^+$, osteoclast$^-$ $^{32}$P-labelled cDNA probe.

The cDNA library produced from the giant cell tumor of the bone was then screened in duplicate for hybridization to the cDNA probes: one screen was performed with the giant cell tumor cDNA probe (stromal cell$^+$, osteoclast$^+$), while a duplicate screen was performed using the cultured stromal cell cDNA probe (stromal cell$^+$, osteoclast$^-$). Hybridization to a stromal$^+$, osteoclast$^+$ probe, accompanied by failure to hybridize to a stromal$^+$, osteoclast$^-$ probe indicated that a clone contained nucleic acid sequences specifically expressed by osteoclasts.

In another embodiment, genomic DNA encoding osteoclast -specific or -related gens products is identified through known hybridization techniques or amplification techniques. In one embodiment, the present invention relates to a method of identifying DNA encoding an osteoclast-specific or -related protein, or gene product, by screening a cDNA library or a genomic DNA library with a DNA probe comprising one or more sequences selected from the group consisting of the DNA sequences set out in Table I (SEQ ID NOs: 1–32). Finally, the present invention relates to an osteoclast-specific or -related protein encoded by a nucleotide sequence comprising a DNA sequence selected from the group consisting of the sequences set out in Table I, or their complementary strands.

BRIEF DESCRIPTION OF THE FIGURE

The Figure shows the cDNA sequence (SEQ ID NO: 33) of human gelatinase B, and highlights those portions of the sequence represented by the osteoclast-specific or -related cDNA clones of the present invention.

DETAILED DESCRIPTION OF THE INVENTION

As described herein, Applicant has identified osteoclast-specific or osteoclast-related nucleic acid sequences. These sequences were identified as follows: Human giant cell tumor of the bone was used to 1) construct a cDNA library; 2) produce $^{32}$P-labelled cDNA to use as a stromal cell$^+$, osteoclast$^+$ probe, and 3) produce (by culturing) a stromal cell population lacking osteoclasts. The presence of osteoclasts in the giant cell tumor was confirmed by histological staining for the osteoclast marker, type 5 acid phosphatase (TRAP). In addition, monoclonal antibody reagents were used to characterize the multinucleated cells in the giant cell tumor, which cells were found to have a phenotype distinct from macrophages and consistent with osteoclasts.

The stromal cell population lacking osteoclasts was produced by dissociating cells of a giant cell tumor, then growing the cells in tissue culture for at least five passages. After five passages the cultured cell population was homogeneous and appeared fibroblastic. The cultured population contained no multinucleated cells at this point, tested negative for type 5 acid phosphatase, and tested variably alkaline phosphatase positive. That is, the cultured stromal cell population did not contain osteoclasts. The cultured stromal cells were then used to produce a stromal cell$^+$, osteoclast$^-$ $^{32}$P-labelled cDNA probe.

The cDNA library produced from the giant cell tumor of the bone was then screened in duplicate for hybridization to the cDNA probes: one screen was performed with the giant cell tumor cDNA probe (stromal cell⁺, osteoclast⁺), while a duplicate screen was performed using the cultured stromal cell cDNA probe (stromal cell⁺, osteoclast⁻) Clones that hybridized to the giant cell tumor cDNA probe (stromal⁺, osteoclast⁺), but not to the stromal cell cDNA probe (stromal⁺, osteoclast⁻), were assumed to contain nucleic acid sequences specifically expressed by osteoclasts.

As a result of the differential screen described herein, DNA specifically expressed in osteoclast cells characterized as described herein was identified. This DNA, and equivalent DNA sequences, is referred to herein as osteoclast-specific or osteoclast-related DNA. Osteoclast-specific or -related DNA of the present invention can be obtained from sources in which it occurs in nature, can be produced recombinantly or synthesized, chemically; it can be cDNA, genomic DNA, recombinantly-produced DNA or chemically-produced DNA. An equivalent DNA sequence is one which hybridizes, under standard hybridization conditions, to an osteoclast-specific or -related DNA identified as described herein or to a complement thereof.

Differential screening of a human osteoclastoma cDNA library was performed to identify genes specifically expressed in osteoclasts. Of 12,000 clones screened, 195 clones were identified which are either uniquely expressed in osteoclasts, or are osteoclast-related. These clones were further identified as osteoclast-specific, as evidenced by failure to hybridize to mRNA derived from a variety of unrelated human cell types, including epithelium, fibroblasts, lymphocytes, myelomonocytic cells, osteoblasts, and neuroblastoma cells. Of these, 32 clones contain novel cDNA sequences which were not found in the GenBank database.

A large number of cDNA clones obtained by this procedure were found to represent 92 kDa type. IV collagenase (gelatinass B; E. C. 3.4.24.35) as well as tartrate resistant acid phosphatase. In situ hybridization localized mRNA for gelatinass B to multinucleated giant cells in human osteoclastomas. Gelatinass B immunoreactivity was demonstrated in giant. cells from 8/8 osteoclastomas, osteoclasts in normal bone, and in osteoclasts of Paget's disease by use of a polyclonal antisera raised against a synthetic gelatinass B peptide. In contrast, no immunoreactivity for 72 kDa type IV collagenase (gelatinass A; E. C. 3.4.24.24), which is the product of a separate gens, was detected in osteoclastomas or normal osteoclasts.

The present invention has utility for the production and identification of nucleic acid probes useful for identifying osteoclast-specific or -related DNA. Osteoclast-specific or -related DNA of the present invention can be used to identify osteoclast-specific or -related gens products useful in the therapeutic treatment of disorders involving aberrant bone resorption. The osteoclast-specific or -related sequences are also useful for generating peptides which can then be used to produce antibodies useful for identifying osteoclast-specific or -related gens products, or for altering the activity of osteoclast-specific or -related gens products. Such antibodies are referred to as osteoclast-specific antibodies. Osteoclast-specific antibodies are also useful for identifying osteoclasts. Finally, osteoclast -specific or -related DNA sequences of the present invention are useful in gens therapy. For example, they can be used to alter the expression in osteoclasts of an aberrant osteoclast -specific or -related gens product or to correct aberrant expression of an osteoclast-specific or -related gens product. The sequences described herein can further be used to cause osteoclast-specific or -related gene expression in cells in which such expression does not ordinarily occur, i.e., in cells which are not osteoclasts.

EXAMPLE 1

Osteoclast cDNA Library construction

Messenger RNA (mRNA) obtained from a human osteoclastoma ('giant cell tumor of bone'), was used to construct an osteoclastoma cDNA library. Osteoclastomas are actively bone resorptive tumors, but are usually non-metastatic. In cryostat sections, osteoclastomas consist of ~30% multinucleated cells positive for tartrate resistant acid phosphatase (TRAP), a widely utilized phenotypic marker specific in vivo for osteoclasts (Minkin, Calcif. Tissue Int. 34:285–290 (1982)). The remaining cells are uncharacterized 'stromal' cells, a mixture of cell types with fibroblastic/ mesenchymal morphology. Although it has not yet been definitively shown, it is generally held that the osteoclasts in these tumors are non-transformed, and are activated to resorb bone in vivo by substance(s) produced by the stromal cell element.

Monoclonal antibody reagents were used to partially characterize the surface phenotype of the multinucleated cells in the giant cell tumors of long bone. In frozen sections, all multinucleated cells expressed CD68, which has previously been reported to define an antigen specific for both osteoclasts and macrophages (Horton, M. A. and M. H. Helfrich, In Biology and Physiology of the Osteoclast, B. R. Rifkin and C. V. Gay, editors, CRC Press, Inc. Boca Raton, Fla., 33–54 (1992)). In contrast, no staining of giant cells was observed for CD11b or CD14 surface antigens, which are present on monocyte/macrophages and granulocytes (Arnaout, M. A. et al. J. Cell. physiol. 137:305 (1988); Haziot, A. et al. J. Immunol. 141:547 (1988)). Cytocentrifuge preparations of human peripheral blood monocytes were positive for CD68, CD11b, and CD14. These results demonstrate that the multinucleated giant cells of osteoclastomas have a phenotype which is distinct from that of macrophages, and which is consistent with that of osteoclasts.

Osteoclastoma tissue. was snap frozen in liquid nitrogen and used to prepare poly A⁺ mRNA according to standard methods. cDNA cloning into a pcDNAII vector was carried out using a commercially-available kit (Librarian, InVitrogen). Approximately 2.6×10⁶ clones were obtained, >95% of which contained inserts of an average length 0.6 kB.

EXAMPLE 2

Stromal Cell mRNA Preparation

A portion of each osteoclastoma was snap frozen in liquid nitrogen for mRNA preparation. The remainder of the tumor was dissociated using brief trypsinization and mechanical disaggregation, and placed into tissue culture. These cells were expanded in Dulbecco's MEM (high glucose, Sigma) supplemented with 10% newborn calf serum (MA Bioproducts), gentamycin (0.5 mg/ml), 1-glutamine (2 mM) and non-essential amino acids (0.1 mM) (Gibco). The stromal cell population was passaged at least five times, after which it showed a homogenous, fibroblastic looking cell population that contained no multinucleated cells. The stromal cells were mononuclear, tested negative for acid phosphatase, and tested variably alkaline phosphatase positive. These findings indicate that propagated stromal cells (i.e., stromal cells that are passaged in culture) are non-osteoclastic and non-activated.

EXAMPLE 3

Identification of DNA Encoding Osteoclastoma-Specific or -Related Gene products by Differential screening of an Osteoclastoma cDNA Library A total of 12,000 clones drawn from the osteoclastoma cDNA library were screened by differential hybridization, using mixed $^{32}$P labelled cDNA probes derived from (1) giant cell tumor mRNA (stromal cell$^+$, OC$^+$), and (2) mRNA from stromal cells (stromal cell$^+$, OC$^-$) cultivated from the same tumor. The probes were labelled with $^{32}$[P]dCTP by random priming to an activity of ~10$^9$CPM/µg. Of these 12,000 clones, 195 gave a positive hybridization signal with giant cell (i.e., osteoclast and stromal cell) mRNA, but not with stromal cell mRNA. Additionally, these clones failed to hybridize to cDNA produced from mRNA derived from a variety of unrelated human cellI types including epithelial cells, fibroblasts, lymphocytes, myelomonocytic cells, osteoblasts, and neuroblastoma cells. The failure of these clones to hybridize to cDNA produced from mRNA derived from other cell types supports the conclusion that these clones are either uniquely expressed in osteoclasts, or are osteoclast-related.

The osteoclast (OC) cDNA library was screened for differential hybridization to OC cDNA (stromal cell$^+$, OC$^+$) and stromal cell cDNA (stromal cell$^+$, OC$^-$) as follows:

NYTRAN filters (Schleicher & Schuell) were placed on agar plates containing growth medium and ampicillin. Individual bacterial colonies from the OC library were randomly picked and transferred, in triplicate, onto filters with preruled grids and then onto a master agar plate. Up to 200 colonies were inoculated onto a single 90-mm filter/plate using these techniques. The plates were inverted and incubated at 37° C. until the bacterial inoculates had grown (on the filter) to a diameter of 0.5–1.0 mm.

The colonies were then lysed, and the DNA bound to the filters by first placing the filters on top of two pieces of Whatman 3MM paper saturated with 0.5N NaOH for 5 minutes. The filters were neutralized by placing on two pieces of Whatman 3MM paper saturated with 1M Tris-HCL, pH 8.0 for 3–5 minutes. Neutralization was followed by incubation on another set of Whatman 3MM papers saturated with 1M Tris-HCL, pH 8.0/1.5M NaCl for 3–5 minutes. The filters were then washed briefly in 2× SSC.

DNA was immobilized on the filters by baking the filters at 80° C. for 30 minutes. Filters were best used immediately, but they could be stored for up to one week in a vacuum jar at room temperature.

Filters were prehybridized in 5–8 ml of hybridization solution per filter, for 2–4 hours in a heat sealable bag. An additional 2 ml of solution was added for each additional filter added to the hybridization bag. The hybridization buffer consisted of 5× SSC, 5×Denhardt's solution, 1% SDS and 100 µg/ml denatured heterologous DNA.

Prior to hybridization, labeled probe was denatured by heating in 1× SSC for 5 minutes at 100° C., then immediately chilled on ice. Denatured probe was added to the filters in hybridization solution, and the filters hybridized with continuous agitation for 12–20 hours at 65° C.

After hybridization, the filters were washed in 2× SSC/0.2% SDS at 50°–60° C. for 30 minutes, followed by washing in 0.2× SSC/0.2% SDS at 60° C. for 60 minutes.

The filters were then air dried and autoradiographed using an intensifying screen at −70° C. overnight.

EXAMPLE 4

DNA Sequencing of Selected Clones

Clones reactive with the mixed tumor probe, but unreactive with the stromal cell probe, are expected to contain either osteoclast-related, or in vivo 'activated' stromal-cell-related gene products. One hundred and forty-four cDNA clones that hybridized to tumor cell cDNA, but not to stromal cell cDNA, were sequenced by the dideoxy chain termination method of Sanger et al. (Sanger F., et al. Proc. Natl. Acad. Sci. USA 74:5463 (1977)) using sequenase (US Biochemical). The DNASIS (Hitatchi) program was used to carry out sequence analysis and a homology search in the GenBank/EMBL database.

Fourteen of the 195 tumor$^+$ stromal$^-$ clones were identified as containing inserts with a sequence identical to the osteoclast marker, type 5 tartrate-resistant acid phosphatase (TRAP) (GenBank accession number J04430 M19534). The high representation of TRAP positive clones also indicates the effectiveness of the screening procedure in enriching for clones which contain osteoclast-specific or related cDNA sequences.

Interestingly, an even larger proportion of the tumor$^+$ stromal$^-$ clones (77/195; 39.5%) were identified as human gelatinase B (macrophage-derived gelatinase) (Wilhelm, S. M. J. Biol. Chem. 264:17213 (1989)), again indicating high expression of this enzyme by osteoclasts. Twenty-five of the gelatinase B clones were identified by dideoxy sequence analysis; all 25 showed 100% sequence homology to the published gelatinase B sequence (Genbank accession number J05070). The portions of the gelatinase B cDNA sequence covered by these clones is shown in the Figure (SEQ ID NO: 33). An additional 52 gelatinase B clones were identified by reactivity with a $^{32}$P-labelled probe for gelatinase B.

Thirteen of the sequenced clones yielded no readable sequence. A DNASIS search of GenBank/EMBL databases revealed that, of the remaining 91 clones, 32 clones contain novel sequences which have not yet been reported in the databases or in the literature. These partial sequences are presented in Table I. Note that three of these sequences were repeats, indicating fairly frequent representation of mRNA related to this sequence. The repeat sequences are indicated by $^{a,b}$, superscripts (Clones 198B, 223B and 32C of Table I).

TABLE I

PARTIAL SEQUENCES OF 32 NOVEL OC-SPECIFIC OR -RELATED
EXPRESSED GENES (cDNA CLONES)

34A (SEQ ID NO: 1)

| 1 | GCAAATATCT | AAGTTTATTG | CTTGGATTTC | TAGTGAGAGC | TGTTGAATTT | GGTGATGTCA |
|---|---|---|---|---|---|---|
| 61 | AATGTTTCTA | GGGTTTTTTT | AGTTTGTTTT | TATTGAAAAA | TTTAATTATT | TATGCTATAG |
| 121 | GTGATATTCT | CTTTGAATAA | ACCTATAATA | GAAAATAGCA | GCAGACAACA | |

4B (SEQ ID NO: 2)

| 1 | GTGTCAACCT | GCATATCCTA | AAAATGTCAA | AATGCTGCAT | CTGGTTAATG | TCGGGGTAGG |
|---|---|---|---|---|---|---|
| 61 | GGG | | | | | |

12B (SEQ ID NO: 3)

| 1 | CTTCCCTCTC | TTGCTTCCCT | TTCCCAAGCA | GAGGTGCTCA | CTCCATGGCC | ACCGCCACCA |
|---|---|---|---|---|---|---|
| 61 | CAGGCCCACA | GGGAGTACTG | CCAGACTACT | GCTGATGTTC | TCTTAAGGCC | CAGGGAGTCT |
| 121 | CAACCAGCTG | GTGGTGAATG | CTGCCTGGCA | CGGGACCCCC | CCC | |

TABLE I-continued

PARTIAL SEQUENCES OF 32 NOVEL OC-SPECIFIC OR -RELATED
EXPRESSED GENES (cDNA CLONES)

28B (SEQ ID NO: 4)

| | | | | | |
|---|---|---|---|---|---|
| 1   | TTTTATTTGT | AAATATATGT | ATTACATCCC | TAGAAAAAGA | ATCCCAGGAT | TTTCCCTCCT |
| 61  | GTGTGTTTTC | GTCTTGCTTC | TTCATGGTCC | ATGATGCCAG | CTGAGGTTGT | CAGTACAATG |
| 121 | AAACCAAACT | GGCGGGATGG | AAGCAGATTA | TTCTGCCATT | TTTCCAGGTC | TTT |

37B (SEQ ID NO: 5)

| | | | | | |
|---|---|---|---|---|---|
| 1   | GGCTGGACAT | GGGTGCCCTC | CACGTCCCTC | ATATCCCCAG | GCACACTCTG | GCCTCAGGTT |
| 61  | TTGCCCTGGC | CATGTCATCT | ACCTGGAGTG | GGCCCTCCCC | TTCTTCAGCC | TTGAATCAAA |
| 121 | AGCCACTTTG | TTAGGCGAGG | ATTTCCCAGA | CCACTCATCA | CATTAAAAAA | TATTTTGAAA |
| 181 | ACAAAAAAAA | AAAAAAA |

55B (SEQ ID NO: 6)

| | | | | | |
|---|---|---|---|---|---|
| 1   | TTGACAAAGC | TGTTTATTTC | CACCAATAAA | TAGTATATGG | TGATTGGGGT | TTCTATTTAT |
| 61  | AAGAGTAGTG | GCTATTATAT | GGGGTATCAT | GTTGATGCTC | ATAAATAGTT | CATATCTACT |
| 121 | TAATTTGCCT | TC |

60B (SEQ ID NO: 7)

| | | | | | |
|---|---|---|---|---|---|
| 1  | GAAGAGAGTT | GTATGTACAA | CCCCAACAGG | CAAGCACAGCT | AAATGCAGAG | GGTACAGAGA |
| 61 | GATCCCGAGG | GAATT |

86B (SEQ ID NO: 8)

| | | | | | |
|---|---|---|---|---|---|
| 1   | GGATGGAAAC | ATGTAGAAGT | CCAGAGAAAA | ACAATTTTAA | AAAAAGGTGG | AAAAGTTACG |
| 61  | GCAAACCTGA | GATTTCAGCA | TAAAATCTTT | AGTTAGAAGT | GAGAGAAAGA | AGAGGGAGGC |
| 121 | TGGTTGCTGT | TGCACGTATC | AATAGGTTAT | C |

87B (SEQ ID NO: 9)

| | | | | | |
|---|---|---|---|---|---|
| 1   | TTCTTGATCT | TTAGAACACT | ATGAATAGGG | AAAAAAGAAA | AAACTGTTCA | AAATAAAATG |
| 61  | TAGGAGCCGT | GCTTTTGGAA | TGCTTGAGTG | AGGAGCTCAA | CAAGTCCTCT | CCCAAGAAAG |
| 181 | CAATGATAAA | ACTTGACAAA | A |

98B (SEQ ID NO: 10)

| | | | | | |
|---|---|---|---|---|---|
| 1   | ACCCATTTCT | AACAATTTTT | ACTGTAAAAT | TTTTGGTCAA | AGTTCTAAGC | TTAATCACAT |
| 61  | CTCAAAGAAT | AGAGGCAATA | TATAGCCCAT | CTTACTAGAC | ATACAGTATT | AAACTGGACT |
| 121 | GAATATGAGG | ACAAGCTCTA | GTGGTCATTA | AACCCCTCAG | AA |

110B (SEQ ID NO: 11)

| | | | | | |
|---|---|---|---|---|---|
| 1   | ACATATATTA | ACAGCATTCA | TTTGGCCAAA | ATCTACACGT | TTGTAGAATC | CTACTGTATA |
| 61  | TAAAGTGGGA | ATGTATCAAG | TATAGACTAT | GAAAGTGCAA | ATAACAAGTC | AAGGTTAGAT |
| 121 | TAACTTTTTT | TTTTTACATT | ATAAAATTAA | CTTGTTT |

118B (SEQ ID NO: 12)

| | | | | | |
|---|---|---|---|---|---|
| 1  | CCAAATTTCT | CTGGAATCCA | TCCTCCCTCC | CATCACCATA | GCCTCGAGAC | GTCATTTCTG |
| 61 | TTTGACTACT | CCAGC |

133B (SEQ ID NO: 13)

| | | | | | |
|---|---|---|---|---|---|
| 1   | AACTAACCTC | CTCGGACCCC | TGCCTCACTC | ATTTACACCA | ACCACCCAAC | TATCTATAAA |
| 61  | CCTGAGCCAT | GGCCATCCCT | TATGAGCGGC | GCAGTGATTA | TAGGCTTTCG | CTCTAAGATA |
| 121 | AAAT |

140B (SEQ ID NO: 14)

| | | | | | |
|---|---|---|---|---|---|
| 1   | ATTATTATTC | TTTTTTATG | TTAGCTTAGC | CATGCAAAAT | TTACTGGTGA | AGCAGTTAAT |
| 61  | AAAACACACA | TCCCATTGAA | GGGTTTTGTA | CATTTCAGTC | CTTACAAATA | ACAAAGCAAT |
| 121 | GATAAACCCG | GCACGTCCTG | ATAGGAAATT | C |

144B (SEQ ID NO: 15)

| | | | | | |
|---|---|---|---|---|---|
| 1  | CGTGACACAA | ACATGCATTC | GTTTATTCA | TAAAACAGCC | TGGTTTCCTA | AAACAATACA |
| 61 | AACAGCATGT | TCATCAGCAG | GAAGCTGGCC | GTGGGCAGGG | GGGCC |

198B[a] (SEQ ID NO: 16)

| | | | | | |
|---|---|---|---|---|---|
| 1   | ATAGGTTAGA | TTCTCATTCA | CGGGACTAGT | TAGCTTTAAG | CACCCTAGAG | GACTAGGGTA |
| 61  | ATCTGACTTC | TCACTTCCTA | AGTTCCCTCT | TATATCCTCA | AGGTAGAAAT | GTCTATGTTT |
| 121 | TCTACTCCAA | TTCATAAATC | TATTCATAAG | TCTTTGGTAC | AAGTTACATG | ATAAAAAGAA |
| 181 | ATGTGATTTG | TCTTCCCTTC | TTTGCACTTT | TCAAATAAAG | TATTTATCTC | CTGTCTACAG |
| 241 | TTTAAT |

212B (SEQ ID NO: 17)

| | | | | | |
|---|---|---|---|---|---|
| 1   | GTCCAGTATA | AAGGAAAGCG | TTAAGTCGGT | AAGCTAGAGG | ATTGTAAATA | TCTTTTATGT |
| 61  | CCTCTAGATA | AAACACCCGA | TTAACAGATG | TTAACCTTTT | ATGTTTTGAT | TTGCTTTAAA |
| 121 | AATGGCCTTC | TACACATTAG | CTCCAGCTAA | AAAGACACAT | TGAGAGCTTA | GAGGATAGTC |
| 181 | TCTGGAGC |

223B[b] (SEQ ID NO: 18)

| | | | | | |
|---|---|---|---|---|---|
| 1   | GCACTTGGAA | GGGAGTTGGT | GTGCTATTTT | TGAAGCAGAT | GTGGTGATAC | TGAGATTGTC |
| 61  | TGTTCAGTTT | CCCCATTTGT | TTGTGCTTCA | AATGATCCTT | CCTACTTTGC | TTCTCTCCAC |
| 121 | CCATGACCTT | TTTCACTGTG | GCCATCAAGG | ACTTTCCTGA | CAGCTTGTGT | ACTCTTAGGC |

TABLE I-continued

PARTIAL SEQUENCES OF 32 NOVEL OC-SPECIFIC OR -RELATED EXPRESSED GENES (cDNA CLONES)

| | | | | | | |
|---|---|---|---|---|---|---|
| 181 | TAAGAGATGT | GACTACAGCC | TGCCCCTGAC | TG | | |
| 241B (SEQ ID NO: 19) | | | | | | |
| 1 | TGTTAGTTTT | TAGGAAGGCC | TGTCTTCTGG | GAGTGAGGTT | TATTAGTCCA | CTTCTTGGAG |
| 61 | CTAGACGTCC | TATAGTTAGT | CACTGGGGAT | GGTGAAAGAG | GGAGAAGAGG | AAGGGCGAAG |
| 121 | GGAAGGGCTC | TTTGCTAGTA | TCTCCATTTC | TAGAAGATGG | TTTAGATGAT | AACCACAGGT |
| 181 | CTATATGAGC | ATAGTAAGGC | TGT | | | |
| 32C[b] (SEQ ID NO: 20) | | | | | | |
| 1 | CCTATTTCTG | ATCCTGACTT | TGGACAAGGC | CCTTCAGCCA | GAAGACTGAC | AAAGTCATCC |
| 121 | TCCGTCTACC | AGAGCGTGCA | CTTGTGATCC | TAAAATAAGC | TTCATCTCCG | GCTGTGCCTT |
| 161 | GGGTGGAAGG | GGCAGGATTC | TGCAGCTGCT | TTTGCATTTC | TCTTCCTAAA | TTTCATT |
| 34C (SEQ ID NO: 21) | | | | | | |
| 1 | CGGAGCGTAG | GTGTGTTTAT | TCCTGTACAA | ATCATTACAA | AACCAAGTCT | GGGGCAGTCA |
| 61 | CCGCCCCCAC | CCATCACCCC | AGTGCAATCG | CTAGCTGCTG | GCCTTT | |
| 47C (SEQ ID NO: 22) | | | | | | |
| 1 | TTAGTTCAGT | CAAAGCAGGC | AACCCCCTTT | GGCACTGCTG | CCACTGGGGT | CATGGCGGTT |
| 61 | GTGGCAGCTG | GGGAGGTTTC | CCCAACACCC | TCCTCTGCTT | CCCTGTGTGT | CGGGGTCTCA |
| 121 | GGAGCTGACC | CAGAGTGGA | | | | |
| 65C (SEQ ID NO: 23) | | | | | | |
| 1 | GCTGAATGTT | TAAGAGAGAT | TTTGGTCTTA | AAGGCTTCAT | CATGAAAGTG | TACATGCATA |
| 61 | TGCAAGTGTG | AATTACGTGG | TATGGATGGT | TGCTTGTTTA | TTAACTAAAG | ATGTACAGCA |
| 121 | AACTGCCCGT | TTAGAGTCCT | CTTAATATTG | ATGTCCTAAC | ACTGGGTCTG | CTTATGC |
| 79C (SEQ ID NO: 24) | | | | | | |
| 1 | GGCAGTGGGA | TATGGAATCC | AGAAGGGAAA | CAAGCACTGG | ATAATTAAAA | ACAGCTGGGG |
| 61 | AGAAAACTGG | GGAAACAAAG | GATATATCCT · | CATGGCTCGA | AATAAGAACA | ACGCCTGTGG |
| 121 | CATTGCCAAC | CTGGCCAGCT | TCCCCAAGAT | GTGACTCCAG | CCAGAAA | |
| 84C (SEQ ID NO: 25) | | | | | | |
| 1 | GCCAGGGCGG | ACCGTCTTTA | TTCCTCTCCT | GCCTCAGAGG | TCAGGAAGGA | GGTCTGGCAG |
| 61 | GACCTGCAGT | GGGCCCTAGT | CATCTGTGGC | AGCGAAGGTG | AAGGGACTCA | CCTTGTCGCC |
| 121 | CGTGCCTGAG | TAGAACTTGT | TCTGGAATTC | C | | |
| 86C (SEQ ID NO: 26) | | | | | | |
| 1 | AACTCTTTCA | CACTCTGGTA | TTTTTAGTTT | AACAATATAT | GTGTTGTGTC | TTGGAAATTA |
| 61 | GTTCATATCA | ATTCATATTG | AGCTGTCTCA | TTCTTTTTTT | AATGGTCATA | TACAGTAGTA |
| 121 | TTCAATTATA | AGAATATATC | CTAATACTTT | TTAAAA | | |
| 87C (SEQ ID NO: 27) | | | | | | |
| 1 | GGATAAGAAA | GAAGGCCTGA | GGGCTAGGGG | CCGGGGCTGG | CCTGCGTCTC | AGTCCTGGGA |
| 61 | CGCAGCAGCC | CGCACAGGTT | GAGAGGGGCA | CTTCCTCTTG | CTTAGGTTGG | TGAGGATCTG |
| 121 | GTCCTGGTTG | GCCGGTGGAG | AGCCACAAAA | | | |
| 88C (SEQ ID NO: 28) | | | | | | |
| 1 | CTGACCTTCG | AGAGTTTGAC | CTGGAGCCGG | ATACCTACTG | CCGCTATGAC | TCGGTCAGCG |
| 61 | TGTTCAACGG | AGCCGTGAGC | GACGACTCCG | GTGGGGAAGT | TCTGCGGCGA | T |
| 89C (SEQ ID NO: 29) | | | | | | |
| 1 | ATCCCTGGCT | GTGGATAGTG | CTTTTGTGTA | GCAAATGCTC | CCTCCTTAAG | GTTATAGGGC |
| 61 | TCCCTGAGTT | TGGGAGTGTG | GAAGTACTAC | TTAACTGTCT | GTCCTGCTTG | GCTGTCGTTA |
| 121 | TCGTTTTCTG | GTGATGTTGT | GCTAACAATA | AGAATAC | | |
| 101C (SEQ ID NO: 30) | | | | | | |
| 1 | GGCTGGGCAT | CCCTCTCCTC | CTCCATCCCC | ATACATCACC | AGGTCTAATG | TTTACAAACG |
| 61 | GTGCCAGCCC | GGCTCTGAAG | CCAAGGGCCG | TCCGTGCCAC | GGTGGCTGTG | AGTATTCCTC |
| 121 | CGTTAGCTTT | CCCATAAGGT | TGGAGTATCT | GC | | |
| 112C (SEQ ID NO: 31) | | | | | | |
| 1 | CCAACTCCTA | CCGCGATACA | GACCCACAGA | GTGCCATCCC | TGAGAGACCA | GACCGCTCCC |
| 161 | CAATACTCTC | CTAAAATAAA | CATGAAGCAC | | | |
| 114C (SEQ ID NO: 32) | | | | | | |
| 1 | CATGGATGAA | TGTCTCATGG | TGGGAAGGAA | CATGGTACAT | TTC | |

[a]Repeated 3 times
[b]Repeated 2 times

Sequence analysis of the OC+ stromal cell− cloned DNA sequences revealed, in addition to the novel sequences, a number of previously-described genes. The known genes identified (including type 5 acid phosphatase, gelatinass B, cystatin C (13 clones), Alu repeat sequences (11 clones), creatnine kinass (6 clones) and others) are summarized in Table II. In situ hybridization (described below) directly demonstrated that gelatinass B mRNA is expressed in multinucleated osteoclasts and not in stromal cells. Although gelatinase B is a well-characterized protease, its expression at high levels in osteoclasts has not been previously described. The expression in osteoclasts of cystatin C, a cystsine protease inhibitor, is also unexpected. This finding has not yet been confirmed by in situ hybridization. Taken together, these results demonstrate that most of these identified genes are osteoclast-expressed, thereby confirming the effectiveness of the differential screening strategy for identifying DNA encoding osteoclast-specific or -related gens products. Therefore, novel genes identified by this method have a high probability of being OC-specific or -related.

In addition, a minority of the genes identified by this screen are probably not expressed by OCs (Table II). For example, type III collagen (6 clones), collagen type I (1 clone), dermatansulfate (1 clone), and type VI collagen (1 clone) are more likely to originate from the stromal cells or from osteoblastic cells which are present in the tumor. These cDNA sequences survive the differential screening process either because the cells which produce them in the tumor in vivo die out during the stromal cell propagation phase, or because they stop producing their product in vitro. These clones do not constitute more than 5–10% of the all sequences selected by differential hybridization.

TABLE II

SEQUENCE ANALYSIS OF CLONES ENCODING KNOWN SEQUENCES FROM AN OSTEOCLASTOMA cDNA LIBRARY

| | |
|---|---|
| Clones with Sequence Homology to Collagenase Type IV | 25 total |
| Clones with Sequence Homology to Type 5 Tartrate Resistant Acid Phosphatase | 14 total |
| Clones with Sequence Homology to Cystatin C: | 13 total |
| Clones with Sequence Homology to Alu-repeat Sequences | 11 total |
| Clones with Sequence Homology to Creatnine Kinase | 6 total |
| Clones with Sequence Homology to Type III Collagen | 6 total |
| Clones with Sequence Homology to MHC Class I γ Invariant Chain | 5 total |
| Clones with Sequence Homology to MHC Class II β Chain | 3 total |
| One or Two Clone(s) with Sequence Homology to Each of the Following: | |
| αI collagen type I | |
| γ interferon inducible protein | |
| osteopontin | |
| Human chondroitin/dermatansulfate | |
| α globin | |
| β glucosidase/sphingolipid activator | |
| Human CAPL protein (Ca binding) | |
| Human EST 01024 | |
| Type VI collagen | |
| Human EST 00553 | |
| | 10 total |

EXAMPLE 5

In situ hybridization of OC-Expressed Genes

In situ hybridization was performed using probes derived from novel cloned sequences in order to determine whether the novel putative OC-specific or -related genes are differentially expressed in osteoclasts (and not expressed in the stromal cells) of human giant cell tumors. Initially, in situ hybridization was performed using antisense (positive) and sense (negative control) cRNA probes against human type IV collagenase/gelatinase B labelled with $^{35}$S-UTP.

A thin section of human giant cell tumor reacted with the antisense probe resulted in intense labelling of all OCs, as indicated by the deposition of silver grains over these cells, but failed to label the stromal cell elements. In contrast, only minimal background labelling was observed with the sense (negative control) probe. This result confirmed that gelatinase B is expressed in human OCs.

In situ hybridization was then carried out using cRNA probes derived from 11/32 novel genes, labelled with digoxigenin UTP according to known methods.

The results of this analysis are summarized in Table III. Clones 28B, 118B, 140B, 198B, and 212B all gave positive reactions with OCs in frozen sections of a giant cell tumor, as did the positive control gelatinase B. These novel clones therefore are expressed in OCs and fulfill all criteria for OC-relatedness. 198B is repeated three times, indicating relatively high expression. Clones 4B, 37B, 88C and 98B produced positive reactions with the tumor tissue; however the signal was not well-localized to OCs. These clones are therefore not likely to be useful and are eliminated from further consideration. Clones 86B and 87B failed to give a positive reaction with any cell type, possibly indicating very low level expression. This group of clones could still be useful but may be difficult to study further. The results of this analysis show that 5/11 novel genes are expressed in OCs, indicating that ~50% of novel sequences likely to be OC-related.

To generate probes for the in situ hybridizations, cDNA derived from novel cloned osteoclast-specific or -related cDNA was subcloned into a BlueScript II SK(−) vector. The orientation of cloned inserts was determined by restriction analysis of subclones. The T7 and T3 promoters in the BlueScriptII vector was used to generate $^{35}$S-labelled ($^{35}$S-UTP, 850 Ci/mmol, Amersham, Arlington Heights, Ill.), or UTP digoxygenin labelled cRNA probes.

TABLE III

In Situ HYBRIDIZATION USING PROBES DERIVED FROM NOVEL SEQUENCES

| | Reactivity with: | |
|---|---|---|
| Clone | Osteoclasts | Stromal Cells |
| 4B | + | + |
| 28B* | + | − |
| 37B | + | + |
| 86B | − | − |
| 87B | − | − |
| 88C | + | + |
| 98B | + | + |
| 118B* | + | − |
| 140B* | + | − |
| 198B* | + | − |
| 212B* | + | − |
| Gelatinase B* | + | − |

*OC-expressed, as indicated by reactivity with antisense probe and lack of reactivity with sense probe on OCs only.

In situ hybridization was carried out on 7 micron cryostat sections of a human osteoclastoma as described previously (Chang, L.-C. et al. Cancer Res, 49:6700 (1989)). Briefly, tissue was fixed in 4% paraformaldehyde and embedded in OCT (Miles Inc., Kankakee, Ill. The sections were rehydrated, postfixed in 4% paraformaldehyde, washed, and pretreated with 10 mM DTT, 10mM iodoacetamide, 10 mM N-ethylmaleimide and 0.1 triethanolamtne-HCL. Prehybridization was done with 50% deionized formamide, 10 mM Tris-HCl, pH 7.0, 1×Denhardt's, 500 mg/ml tRNA, 80 mg/ml salmon sperm DNA, 0.3M NaCl, 1 mM EDTA, and 100 mM DTT at 45° C. for 2 hours. Fresh hybridization solution containing 10% dextran sulfate and 1.5 ng/ml $^{35}$S-labelled or digoxigenin labelled RNA probe was applied after heat denaturation. Sections were coverslipped and then incubated in a moistened chamber at 45°–50° C. overnight. Hybridized sections were washed four times with 50% formamide, 2× SSC, containing 10 mM DTT and 0.5% Triton X-100 at 45° C. Sections were treated with RNase A and RNase T1 to digest single-stranded RNA, washed four times in 2× SSC/10 mM DTT.

In order to detect $^{35}$S-labelling by autoradiography, slides were dehydrated, dried, and coated with Kodak NTB-2 emulsion. The duplicate slides were split, and each set was placed in a black box with desiccant, sealed, and incubated at 4° C. for 2 days. The slides were developed (4 minutes) and fixed (5 minutes) using Kodak developer D19 and Kodak fixer. Hematoxylin and eosin were used as counterstains.

In order to detect digoxygenin-labelled probes, a Nucleic Acid Detection Kit (Boehringer-Mannheim, Cat. #1175041) was used. Slides were washed in Buffer 1 consisting of 100 mM Tris/150 mM NaCl, pH7.5, for 1 minute. 100 µl Buffer 2 was added (made by adding 2 mg/ml blocking reagent as provided by the manufacturer) in Buffer 1 to each slide. The slides were placed on a shaker and gently swirled at 20° C.

Antibody solutions were diluted 1:100 with Buffer 2 (as provided by the manufacturer). 100 µl of diluted antibody solution was applied to the slides and the slides were then incubated in a chamber for 1 hour at room temperature. The slides were monitored to avoid drying. After incubation with antibody solution, slides were washed in Buffer 1 for 10 minutes, then washed in Buffer 3 containing 2 mM levamisole for 2 minutes.

After washing, 100 µl color solution was added to the slides. Color solution consisted of nitroblue/tetrazolium salt (NBT) (1:225 dilution) 4.5 µl, 5-bromo-4-chloro-3-indolyl phosphate (1:285 dilution) 3.5 µl, levamisole 0.2 mg in Buffer 3 (as provided by the manufacturer) in a total volume of 1 ml. Color solution was prepared immediately before use.

After adding the color solution, the slides were placed in a dark, humidified chamber at 20° C. for 2–5 hours and monitored for color development. The color reaction was stopped by rinsing slides in TE Buffer.

The slides were stained for 60 seconds in 0.25% methyl green, washed with tap water, then mounted with water-based Permount (Fisher).

EXAMPLE 6

Immunohistochemistry

Immunohistochemical staining was performed on frozen and paraffin embedded tissues as well as on cytospin preparations (see Table IV). The following antibodies were used: polyclonal rabbit anti-human gelatinase antibodies; Ab110 for gelatinase B; monoclonal mouse anti-human CD68 antibody (clone KP1) (DAKO, Denmark); Mo1 (anti-CD11b) and Mo2 (anti-CD14) derived from ATCC cell lines HB CRL 8026 and TIB 228/HB44. The anti-human gelatinase B antibody Ab110 was raised against a synthetic peptide with the amino acid sequence EALMYPMYRFTEGPPLHK (SEQ ID NO: 34), which is specific for human gelatinase B (Corcoran, M. L. et al. *J. Biol. Chem.* 267:515 (1992)).

Detection of the immunohistochemical staining was achieved by using a goat anti-rabbit glucose oxidase kit (Vector Laboratories, Burlingame Calif.) according to the manufacturer's directions. Briefly, the sections were rehydrated and pretested with either acetone or 0.1% trypsin. Normal goat serum was used to block nonspecific binding. Incubation with the primary antibody for 2 hours or overnight (Ab110: 1/500 dilution) was followed by either a glucose oxidase labeled secondary anti-rabbit serum, or, in the case of the mouse monoclonal antibodies, were reacted with purified rabbit anti-mouse Ig before incubation with the secondary antibody.

Paraffin embedded and frozen sections from osteoclastomas (GCT) were reacted with a rabbit antiserum against gelatinase B (antibody 110) (Corcoran, M. L. et al. *J. Biol. Chem.* 267:515 (1992)), followed by color development with glucose oxidase linked reagents. The osteoclasts of a giant cell tumor were uniformly strongly positive for gelatinase B, whereas the stromal cells were unreactive. Control sections reacted with rabbit preimmune serum were negative. Identical findings were obtained for all 8 long bone giant cell tumors tested (Table IV). The osteoclasts present in three out of four central giant cell granulomas (GCG) of the mandible were also positive for gelatinase B expression. These neoplasms are similar but not identical to the long bone giant cell tumors, apart from their location in the jaws (Shafer, W. G. et al., Textbook of Oral Pathology, W. B. Saunders Company, Philadelphia, pp. 144–149 (1983)). In contrast, the multinucleated cells from a peripheral giant cell tumor, which is a generally non-resorptive tumor of oral soft tissue, were unreactive with antibody 110 (Shafer, W. G. et al., Textbook of Oral Pathology, W. B. Saunders Company, Philadelphia, pp. 144–149 (1983)).

Antibody 110 was also utilized to assess the presence of gelatinase B in normal bone (n=3) and in Paget's disease, in which there is elevated bone remodeling and increased osteoclastic activity. Strong staining for gelatinase B was observed in osteoclasts both in normal bone (mandible of a 2 year old), and in Paget's disease. Staining was again absent in controls incubated with preimmune serum. Osteoblasts did not stain in any of the tissue sections, indicating that gelatinase B expression is limited to osteoclasts in bone. Finally, peripheral blood monocytes were also reactive with antibody 110 (Table IV).

TABLE IV

DISTRIBUTION OF GELATINASE B IN VARIOUS TISSUES

| Samples | Antibodies tested Ab 110 gelatinase B |
|---|---|
| GCT frozen (n = 2) | |
| giant cells | + |
| stromal cells | − |
| GCT paraffin (n = 6) | |
| giant cells | + |
| stromal cells | − |
| central GCG (n = 4) | |
| giant cells | + (¾) |
| stromal cells | − |
| peripheral GCT (n-4) | |
| giant cells | − |
| stromal cells | − |
| Paget's disease (n = 1) | |
| osteoclasts | + |
| osteoblasts | − |
| normal bone (n = 3) | |
| osteoclasts | + |
| osteoblasts | − |

TABLE IV-continued

DISTRIBUTION OF GELATINASE B IN VARIOUS TISSUES

| Samples | Antibodies tested<br>Ab 110<br>gelatinase B |
|---|---|
| monocytes<br>(cytospin) | + |

Distribution of gelatinase B in multinucleated giant cells, osteoclasts, osteoblasts and stromal cells in various tissues. In general, paraffin embedded tissues were used for these experiments; exceptions are indicated.

Equivalents

Those skilled in the art will recognize, or be able to ascertain using no more than routine experimentation, many equivalents to the specific embodiments described herein. Such equivalents are intended to be encompassed by the following claims.

---

We claim:

1. An osteoclast-specific or -related protein encoded by a nucleotide sequence comprising a DNA sequence selected from the group consisting of SEQ ID NOS: 1–3 and 5–32.

2. An osteoclast-specific or -related peptide encoded by a nucleotide sequence selected from the group consisting of SEQ ID NOS: 1–3 and 5–32.

3. An osteoclast-specific or -related gene product encoded by a nucleotide sequence selected from the group consisting of SEQ ID NOS: 1–3 and 5–32.

* * * * *

UNITED STATES PATENT AND TRADEMARK OFFICE
CERTIFICATE OF CORRECTION

PATENT NO. : 5,656,728
DATED : Aug. 12, 1997
INVENTOR(S) : Philip Stashenko, Yi-Ping Li and Anne L. Wucherpfennig It is certified that error appears in the above-identified patent and that said Letters Patent is hereby corrected as shown below:

Column 1, line 3,

--- GOVERNMENT FUNDING
This invention was made with Government support under Contract No. DE07378 awarded by the National Institutes of Health, National Institute for Dental Research. The Government has certain rights in the invention.---

Signed and Sealed this

Ninth Day of December, 1997

*Attest:*

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 170 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GCAAATATCT AAGTTTATTG CTTGGATTTC TAGTGAGAGC TGTTGAATTT GGTGATGTCA      60

AATGTTTCTA GGGTTTTTTT AGTTTGTTTT TATTGAAAAA TTTAATTATT TATGCTATAG     120

GTGATATTCT CTTTGAATAA ACCTATAATA GAAATAGCA GCAGACAACA                 170
```

( 2 ) INFORMATION FOR SEQ ID NO:2:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

```
GTGTCAACCT GCATATCCTA AAAATGTCAA AATGCTGCAT CTGGTTAATG TCGGGGTAGG      60

GGG                                                                    63
```

( 2 ) INFORMATION FOR SEQ ID NO:3:

( i ) SEQUENCE CHARACTERISTICS:
        ( A ) LENGTH: 163 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
CTTCCCTCTC TTGCTTCCCT TTCCCAAGCA GAGGTGCTCA CTCCATGGCC ACCGCCACCA      60

CAGGCCCACA GGGAGTACTG CCAGACTACT GCTGATGTTC TCTTAAGGCC CAGGGAGTCT     120

CAACCAGCTG GTGGTGAATG CTGCCTGGCA CGGGACCCCC CCC                       163
```

( 2 ) INFORMATION FOR SEQ ID NO:4:

( i ) SEQUENCE CHARACTERISTICS:
          ( A ) LENGTH: 173 base pairs
          ( B ) TYPE: nucleic acid
          ( C ) STRANDEDNESS: double
          ( D ) TOPOLOGY: linear ( i i ) MOLECULE TYPE: DNA (genomic)

( x i ) SEQUENCE DESCRIPTION: SEQ ID NO:4:

```
TTTTATTTGT  AAATATATGT  ATTACATCCC  TAGAAAAAGA  ATCCAGGAT  TTTCCCTCCT     60
GTGTGTTTTC  GTCTTGCTTC  TTCATGGTCC  ATGATGCCAG  CTGAGGTTGT  CAGTACAATG    120
AAACCAAACT  GGCGGGATGG  AAGCAGATTA  TTCTGCCATT  TTTCCAGGTC  TTT           173
```

( 2 ) INFORMATION FOR SEQ ID NO:5:

( i ) SEQUENCE CHARACTERISTICS:
          ( A ) LENGTH: 197 base pairs
          ( B ) TYPE: nucleic acid
          ( C ) STRANDEDNESS: double
          ( D ) TOPOLOGY: linear ( i i ) MOLECULE TYPE: DNA (genomic)

( x i ) SEQUENCE DESCRIPTION: SEQ ID NO:5:

```
GGCTGGACAT  GGGTGCCCTC  CACGTCCCTC  ATATCCCCAG  GCACACTCTG  GCCTCAGGTT    60
TTGCCCTGGC  CATGTCATCT  ACCTGGAGTG  GGCCCTCCCC  TTCTTCAGCC  TTGAATCAAA   120
AGCCACTTTG  TTAGGCGAGG  ATTTCCCAGA  CCACTCATCA  CATTAAAAAA  TATTTTGAAA   180
ACAAAAAAAA  AAAAAA                                                       197
```

( 2 ) INFORMATION FOR SEQ ID NO:6:

( i ) SEQUENCE CHARACTERISTICS:
          ( A ) LENGTH: 132 base pairs
          ( B ) TYPE: nucleic acid
          ( C ) STRANDEDNESS: double
          ( D ) TOPOLOGY: linear ( i i ) MOLECULE TYPE: DNA (genomic)

( x i ) SEQUENCE DESCRIPTION: SEQ ID NO:6:

```
TTGACAAAGC  TGTTTATTTC  CACCAATAAA  TAGTATATGG  TGATTGGGGT  TTCTATTTAT    60
AAGAGTAGTG  GCTATTATAT  GGGGTATCAT  GTTGATGCTC  ATAAATAGTT  CATATCTACT   120
TAATTTGCCT  TC                                                           132
```

( 2 ) INFORMATION FOR SEQ ID NO:7:

( i ) SEQUENCE CHARACTERISTICS:
          ( A ) LENGTH: 75 base pairs
          ( B ) TYPE: nucleic acid
          ( C ) STRANDEDNESS: double
          ( D ) TOPOLOGY: linear ( i i ) MOLECULE TYPE: DNA (genomic)

( x i ) SEQUENCE DESCRIPTION: SEQ ID NO:7:

```
GAAGAGAGTT  GTATGTACAA  CCCCAACAGG  CAAGGCAGCT  AAATGCAGAG  GGTACAGAGA    60
GATCCCGAGG  GAATT                                                         75
```

( 2 ) INFORMATION FOR SEQ ID NO:8:

( i ) SEQUENCE CHARACTERISTICS:

(A) LENGTH: 151 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:8:

| | | | | | | |
|---|---|---|---|---|---|---|
| GGATGGAAAC | ATGTAGAAGT | CCAGAGAAAA | ACAATTTTAA | AAAAAGGTGG | AAAAGTTACG | 60 |
| GCAAACCTGA | GATTTCAGCA | TAAAATCTTT | AGTTAGAAGT | GAGAGAAAGA | AGAGGGAGGC | 120 |
| TGGTTGCTGT | TGCACGTATC | AATAGGTTAT | C | | | 151 |

(2) INFORMATION FOR SEQ ID NO:9:

(i) SEQUENCE CHARACTERISTICS:
(A) LENGTH: 141 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:9:

| | | | | | | |
|---|---|---|---|---|---|---|
| TTCTTGATCT | TTAGAACACT | ATGAATAGGG | AAAAAAGAAA | AAACTGTTCA | AAATAAAATG | 60 |
| TAGGAGCCGT | GCTTTTGGAA | TGCTTGAGTG | AGGAGCTCAA | CAAGTCCTCT | CCCAAGAAAG | 120 |
| CAATGATAAA | ACTTGACAAA | A | | | | 141 |

(2) INFORMATION FOR SEQ ID NO:10:

(i) SEQUENCE CHARACTERISTICS:
(A) LENGTH: 162 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:10:

| | | | | | | |
|---|---|---|---|---|---|---|
| ACCCATTTCT | AACAATTTTT | ACTGTAAAAT | TTTTGGTCAA | AGTTCTAAGC | TTAATCACAT | 60 |
| CTCAAAGAAT | AGAGGCAATA | TATAGCCCAT | CTTACTAGAC | ATACAGTATT | AAACTGGACT | 120 |
| GAATATGAGG | ACAAGCTCTA | GTGGTCATTA | AACCCCTCAG | AA | | 162 |

(2) INFORMATION FOR SEQ ID NO:11:

(i) SEQUENCE CHARACTERISTICS:
(A) LENGTH: 157 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:11:

| | | | | | | |
|---|---|---|---|---|---|---|
| ACATATATTA | ACAGCATTCA | TTTGGCCAAA | ATCTACACGT | TTGTAGAATC | CTACTGTATA | 60 |
| TAAAGTGGGA | ATGTATCAAG | TATAGACTAT | GAAAGTGCAA | ATAACAAGTC | AAGGTTAGAT | 120 |
| TAACTTTTTT | TTTTACATT | ATAAAATTAA | CTTGTTT | | | 157 |

(2) INFORMATION FOR SEQ ID NO:12:

(i) SEQUENCE CHARACTERISTICS:
(A) LENGTH: 75 base pairs
(B) TYPE: nucleic acid
(C) STRANDEDNESS: double
(D) TOPOLOGY: linear ( i i ) MOLECULE TYPE: DNA (genomic)

( x i ) SEQUENCE DESCRIPTION: SEQ ID NO:12:

| | | | | | |
|---|---|---|---|---|---|
| CCAAATTTCT | CTGGAATCCA | TCCTCCCTCC | CATCACCATA | GCCTCGAGAC | GTCATTTCTG | 60 |
| TTTGACTACT | CCAGC | | | | | 75 |

( 2 ) INFORMATION FOR SEQ ID NO:13:

( i ) SEQUENCE CHARACTERISTICS:
        ( A ) LENGTH: 124 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

| | | | | | |
|---|---|---|---|---|---|
| AACTAACCTC | CTCGGACCCC | TGCCTCACTC | ATTTACACCA | ACCACCCAAC | TATCTATAAA | 60 |
| CCTGAGCCAT | GGCCATCCCT | TATGAGCGGC | GCAGTGATTA | TAGGCTTTCG | CTCTAAGATA | 120 |
| AAAT | | | | | | 124 |

( 2 ) INFORMATION FOR SEQ ID NO:14:

( i ) SEQUENCE CHARACTERISTICS:
        ( A ) LENGTH: 151 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:14:

| | | | | | |
|---|---|---|---|---|---|
| ATTATTATTC | TTTTTTTATG | TTAGCTTAGC | CATGCAAAAT | TTACTGGTGA | AGCAGTTAAT | 60 |
| AAAACACACA | TCCCATTGAA | GGGTTTTGTA | CATTTCAGTC | CTTACAAATA | ACAAAGCAAT | 120 |
| GATAAACCCG | GCACGTCCTG | ATAGGAAATT | C | | | 151 |

( 2 ) INFORMATION FOR SEQ ID NO:15:

( i ) SEQUENCE CHARACTERISTICS:
        ( A ) LENGTH: 105 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

| | | | | | |
|---|---|---|---|---|---|
| CGTGACACAA | ACATGCATTC | GTTTTATTCA | TAAAACAGCC | TGGTTTCCTA | AAACAATACA | 60 |
| AACAGCATGT | TCATCAGCAG | GAAGCTGGCC | GTGGGCAGGG | GGGCC | | 105 |

( 2 ) INFORMATION FOR SEQ ID NO:16:

( i ) SEQUENCE CHARACTERISTICS:
        ( A ) LENGTH: 246 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:16:

| | | | | | |
|---|---|---|---|---|---|
| ATAGGTTAGA | TTCTCATTCA | CGGGACTAGT | TAGCTTTAAG | CACCCTAGAG | GACTAGGGTA | 60 |
| ATCTGACTTC | TCACTTCCTA | AGTTCCCTCT | TATATCCTCA | AGGTAGAAAT | GTCTATGTTT | 120 |

```
TCTACTCCAA  TTCATAAATC  TATTCATAAG  TCTTTGGTAC  AAGTTACATG  ATAAAAAGAA         180

ATGTGATTTG  TCTTCCCTTC  TTTGCACTTT  TGAAATAAAG  TATTTATCTC  CTGTCTACAG         240

TTTAAT                                                                        246
```

( 2 ) INFORMATION FOR SEQ ID NO:17:

( i ) SEQUENCE CHARACTERISTICS:
        ( A ) LENGTH: 188 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:17:

```
GTCCAGTATA  AAGGAAAGCG  TTAAGTCGGT  AAGCTAGAGG  ATTGTAAATA  TCTTTTATGT          60

CCTCTAGATA  AACACCCGA  TTAACAGATG  TTAACCTTTT  ATGTTTGAT   TTGCTTTAAA         120

AATGGCCTTC  TACACATTAG  CTCCAGCTAA  AAAGACACAT  TGAGAGCTTA  GAGGATAGTC         180

TCTGGAGC                                                                      188
```

( 2 ) INFORMATION FOR SEQ ID NO:18:

( i ) SEQUENCE CHARACTERISTICS:
        ( A ) LENGTH: 212 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:18:

```
GCACTTGGAA  GGGAGTTGGT  GTGCTATTTT  TGAAGCAGAT  GTGGTGATAC  TGAGATTGTC          60

TGTTCAGTTT  CCCCATTTGT  TTGTGCTTCA  AATGATCCTT  CCTACTTTGC  TTCTCTCCAC         120

CCATGACCTT  TTTCACTGTG  GCCATCAAGG  ACTTTCCTGA  CAGCTTGTGT  ACTCTTAGGC         180

TAAGAGATGT  GACTACAGCC  TGCCCCTGAC  TG                                        212
```

( 2 ) INFORMATION FOR SEQ ID NO:19:

( i ) SEQUENCE CHARACTERISTICS:
        ( A ) LENGTH: 203 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:19:

```
TGTTAGTTTT  TAGGAAGGCC  TGTCTTCTGG  GAGTGAGGTT  TATTAGTCCA  CTTCTTGGAG          60

CTAGACGTCC  TATAGTTAGT  CACTGGGGAT  GGTGAAAGAG  GGAGAAGAGG  AAGGGCGAAG         120

GGAAGGGCTC  TTTGCTAGTA  TCTCCATTTC  TAGAAGATGG  TTTAGATGAT  AACCACAGGT         180

CTATATGAGC  ATAGTAAGGC  TGT                                                   203
```

( 2 ) INFORMATION FOR SEQ ID NO:20:

( i ) SEQUENCE CHARACTERISTICS:
        ( A ) LENGTH: 177 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:20:

| | | | | | |
|---|---|---|---|---|---|
| CCTATTTCTG | ATCCTGACTT | TGGACAAGGC | CCTTCAGCCA | GAAGACTGAC | AAAGTCATCC | 60
| TCCGTCTACC | AGAGCGTGCA | CTTGTGATCC | TAAAATAAGC | TTCATCTCCG | GCTGTGCCTT | 120
| GGGTGGAAGG | GGCAGGATTC | TGCAGCTGCT | TTTGCATTTC | TCTTCCTAAA | TTTCATT | 177

( 2 ) INFORMATION FOR SEQ ID NO:21:

( i ) SEQUENCE CHARACTERISTICS:
        ( A ) LENGTH: 106 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:21:

| | | | | | |
|---|---|---|---|---|---|
| CGGAGCGTAG | GTGTGTTTAT | TCCTGTACAA | ATCATTACAA | AACCAAGTCT | GGGGCAGTCA | 60
| CCGCCCCAC | CCATCACCCC | AGTGCAATGG | CTAGCTGCTG | GCCTTT | | 106

( 2 ) INFORMATION FOR SEQ ID NO:22:

( i ) SEQUENCE CHARACTERISTICS:
        ( A ) LENGTH: 139 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:22:

| | | | | | |
|---|---|---|---|---|---|
| TTAGTTCAGT | CAAAGCAGGC | AACCCCTTT | GGCACTGCTG | CCACTGGGGT | CATGGCGGTT | 60
| GTGGCAGCTG | GGAGGTTTC | CCCAACACCC | TCCTCTGCTT | CCCTGTGTGT | CGGGGTCTCA | 120
| GGAGCTGACC | CAGAGTGGA | | | | | 139

( 2 ) INFORMATION FOR SEQ ID NO:23:

( i ) SEQUENCE CHARACTERISTICS:
        ( A ) LENGTH: 177 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:23:

| | | | | | |
|---|---|---|---|---|---|
| GCTGAATGTT | TAAGAGAGAT | TTTGGTCTTA | AAGGCTTCAT | CATGAAAGTG | TACATGCATA | 60
| TGCAAGTGTG | AATTACGTGG | TATGGATGGT | TGCTTGTTTA | TTAACTAAAG | ATGTACAGCA | 120
| AACTGCCCGT | TTAGAGTCCT | CTTAATATTG | ATGTCCTAAC | ACTGGGTCTG | CTTATGC | 177

( 2 ) INFORMATION FOR SEQ ID NO:24:

( i ) SEQUENCE CHARACTERISTICS:
        ( A ) LENGTH: 167 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:24:

| | | | | | |
|---|---|---|---|---|---|
| GGCAGTGGGA | TATGGAATCC | AGAAGGGAAA | CAAGCACTGG | ATAATTAAAA | ACAGCTGGGG | 60
| AGAAAACTGG | GGAAACAAAG | GATATATCCT | CATGGCTCGA | AATAAGAACA | ACGCCTGTGG | 120

CATTGCCAAC CTGGCCAGCT TCCCCAAGAT GTGACTCCAG CCAGAAA                                167

( 2 ) INFORMATION FOR SEQ ID NO:25:

( i ) SEQUENCE CHARACTERISTICS:
        ( A ) LENGTH: 151 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:25:

GCCAGGGCGG ACCGTCTTTA TTCCTCTCCT GCCTCAGAGG TCAGGAAGGA GGTCTGGCAG            60

GACCTGCAGT GGGCCCTAGT CATCTGTGGC AGCGAAGGTG AAGGGACTCA CCTTGTCGCC           120

CGTGCCTGAG TAGAACTTGT TCTGGAATTC C                                          151

( 2 ) INFORMATION FOR SEQ ID NO:26:

( i ) SEQUENCE CHARACTERISTICS:
        ( A ) LENGTH: 156 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:26:

AACTCTTTCA CACTCTGGTA TTTTAGTTT AACAATATAT GTGTTGTGTC TTGGAAATTA             60

GTTCATATCA ATTCATATTG AGCTGTCTCA TTCTTTTTT AATGGTCATA TACAGTAGTA           120

TTCAATTATA AGAATATATC CTAATACTTT TTAAAA                                    156

( 2 ) INFORMATION FOR SEQ ID NO:27:

( i ) SEQUENCE CHARACTERISTICS:
        ( A ) LENGTH: 150 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:27:

GGATAAGAAA GAAGGCCTGA GGGCTAGGGG CCGGGGCTGG CCTGCGTCTC AGTCCTGGGA            60

CGCAGCAGCC CGCACAGGTT GAGAGGGGCA CTTCCTCTTG CTTAGGTTGG TGAGGATCTG           120

GTCCTGGTTG GCCGGTGGAG AGCCACAAAA                                           150

( 2 ) INFORMATION FOR SEQ ID NO:28:

( i ) SEQUENCE CHARACTERISTICS:
        ( A ) LENGTH: 212 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:28:

GCACTTGGAA GGGAGTTGGT GTGCTATTTT TGAAGCAGAT GTGGTGATAC TGAGATTGTC            60

TGTTCAGTTT CCCCATTTGT TTGTGCTTCA AATGATCCTT CCTACTTTGC TTCTCTCCAC           120

CCATGACCTT TTTCACTGTG GCCATCAAGG ACTTTCCTGA CAGCTTGTGT ACTCTTAGGC           180

TAAGAGATGT GACTACAGCC TGCCCCTGAC TG                                         212

( 2 ) INFORMATION FOR SEQ ID NO:29:

( i ) SEQUENCE CHARACTERISTICS:
        ( A ) LENGTH: 157 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:29:

```
ATCCCTGGCT  GTGGATAGTG  CTTTTGTGTA  GCAAATGCTC  CCTCCTTAAG  GTTATAGGGC      60
TCCCTGAGTT  TGGGAGTGTG  GAAGTACTAC  TTAACTGTCT  GTCCTGCTTG  GCTGTCGTTA     120
TCGTTTTCTG  GTGATGTTGT  GCTAACAATA  AGAATAC                                157
```

( 2 ) INFORMATION FOR SEQ ID NO:30:

( i ) SEQUENCE CHARACTERISTICS:
        ( A ) LENGTH: 152 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:30:

```
GGCTGGGCAT  CCCTCTCCTC  CTCCATCCCC  ATACATCACC  AGGTCTAATG  TTTACAAACG      60
GTGCCAGCCC  GGCTCTGAAG  CCAAGGGCCG  TCCGTGCCAC  GGTGGCTGTG  AGTATTCCTC     120
CGTTAGCTTT  CCCATAAGGT  TGGAGTATCT  GC                                    152
```

( 2 ) INFORMATION FOR SEQ ID NO:31:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:31:

```
CCAACTCCTA  CCGCGATACA  GACCCACAGA  GTGCCATCCC  TGAGAGACCA  GACCGCTCCC     60
CAATACTCTC  CTAAAATAAA  CATGAAGCAC                                         90
```

( 2 ) INFORMATION FOR SEQ ID NO:32:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:32:

```
CATGGATGAA  TGTCTCATGG  TGGGAAGGAA  CATGGTACAT  TTC                        43
```

( 2 ) INFORMATION FOR SEQ ID NO:33:

( i ) SEQUENCE CHARACTERISTICS:
        ( A ) LENGTH: 2334 base pairs
        ( B ) TYPE: nucleic acid
        ( C ) STRANDEDNESS: double
        ( D ) TOPOLOGY: linear (i i) MOLECULE TYPE: other nucleic acid (x i) SEQUENCE DESCRIPTION: SEQ ID NO:33:

| | | | | | | |
|---|---|---|---|---|---|---|
| AGACACCTCT | GCCCTCACCA | TGAGCCTCTG | GCAGCCCCTG | GTCCTGGTGC | TCCTGGTGCT | 60 |
| GGGCTGCTGC | TTTGCTGCCC | CCAGACAGCG | CCAGTCCACC | CTTGTGCTCT | TCCCTGGAGA | 120 |
| CCTGAGAACC | AATCTCACCG | ACAGGCAGCT | GGCAGAGGAA | TACCTGTACC | GCTATGGTTA | 180 |
| CACTCGGGTG | GCAGAGATGC | GTGGAGAGTC | GAAATCTCTG | GGGCCTGCGC | TGCTGCTTCT | 240 |
| CCAGAAGCAA | CTGTCCCTGC | CCGAGACCGG | TGAGCTGGAT | AGCGCCACGC | TGAAGGCCAT | 300 |
| GCGAACCCCA | CGGTGCGGGG | TCCCAGACCT | GGGCAGATTC | CAAACCTTTG | AGGGCGACCT | 360 |
| CAAGTGGCAC | CACCACAACA | TCACCTATTG | GATCCAAAAC | TACTCGGAAG | ACTTGCCGCG | 420 |
| GGCGGTGATT | GACGACGCCT | TTGCCCGCGC | CTTCGCACTG | TGGAGCGCGG | TGACGCCGCT | 480 |
| CACCTTCACT | CGCGTGTACA | GCCGGGACGC | AGACATCGTC | ATCCAGTTTG | GTGTCGCGGA | 540 |
| GCACGGAGAC | GGGTATCCCT | TCGACGGGAA | GGACGGGCTC | CTGGCACACG | CCTTTCCTCC | 600 |
| TGGCCCCGGC | ATTCAGGGAG | ACGCCCATTT | CGACGATGAC | GAGTTGTGGT | CCCTGGGCAA | 660 |
| GGGCGTCGTG | GTTCAACTC | GGTTTGGAAA | CGCAGATGGC | GCGGCCTGCC | ACTTCCCCTT | 720 |
| CATCTTCGAG | GGCCGCTCCT | ACTCTGCCTG | CACCACCGAC | GGTCGCTCCG | ACGGGTTGCC | 780 |
| CTGGTGCAGT | ACCACGGCCA | ACTACGACAC | CGACGACCGG | TTTGGCTTCT | GCCCCAGCGA | 840 |
| GAGACTCTAC | ACCCGGGACG | GCAATGCTGA | TGGGAAACCC | TGCCAGTTTC | CATTCATCTT | 900 |
| CCAAGGCCAA | TCCTACTCCG | CCTGCACCAC | GGACGGTCGC | TCCGACGGCT | ACCGCTGGTG | 960 |
| CGCCACCACC | GCCAACTACG | ACCGGGACAA | GCTCTTCGGC | TTCTGCCCGA | CCCGAGCTGA | 1020 |
| CTCGACGGTG | ATGGGGGGCA | ACTCGGCGGG | GGAGCTGTGC | GTCTTCCCCT | TCACTTTCCT | 1080 |
| GGGTAAGGAG | TACTCGACCT | GTACCAGCGA | GGGCCGCGGA | GATGGGCGCC | TCTGGTGCGC | 1140 |
| TACCACCTCG | AACTTTGACA | GCGACAAGAA | GTGGGGCTTC | TGCCCGGACC | AAGGATACAG | 1200 |
| TTTGTTCCTC | GTGGCGGCGC | ATGAGTTCGG | CCACGCGCTG | GGCTTAGATC | ATTCCTCAGT | 1260 |
| GCCGGAGGCG | CTCATGTACC | CTATGTACCG | CTTCACTGAG | GGGCCCCCT | TGCATAAGGA | 1320 |
| CGACGTGAAT | GGCATCCGGC | ACCTCTATGG | TCCTCGCCCT | GAACCTGAGC | CACGGCCTCC | 1380 |
| AACCACCACC | ACACCGCAGC | CCACGGCTCC | CCCGACGGTC | TGCCCCACCG | GACCCCCCAC | 1440 |
| TGTCCACCCC | TCAGAGCGCC | CCACAGCTGG | CCCCACAGGT | CCCCCCTCAG | CTGGCCCCAC | 1500 |
| AGGTCCCCCC | ACTGCTGGCC | CTTCTACGGC | CACTACTGTG | CCTTTGAGTC | CGGTGGACGA | 1560 |
| TGCCTGCAAC | GTGAACATCT | TCGACGCCAT | CGCGGAGATT | GGGAACCAGC | TGTATTTGTT | 1620 |
| CAAGGATGGG | AAGTACTGGC | GATTCTCTGA | GGGCAGGGGG | AGCCGGCCGC | AGGGCCCCTT | 1680 |
| CCTTATCGCC | GACAAGTGGC | CCGCGCTGCC | CCGCAAGCTG | GACTCGGTCT | TTGAGGAGCC | 1740 |
| GCTCTCCAAG | AAGCTTTTCT | TCTTCTCTGG | GCGCCAGGTG | TGGGTGTACA | CAGGCGCGTC | 1800 |
| GGTGCTGGGC | CCGAGGCGTC | TGGACAAGCT | GGGCCTGGGA | GCCGACGTGG | CCCAGGTGAC | 1860 |
| CGGGGCCCTC | CGGAGTGGCA | GGGGGAAGAT | GCTGCTGTTC | AGCGGGCGGC | GCCTCTGGAG | 1920 |
| GTTCGACGTG | AAGGCGCAGA | TGGTGGATCC | CCGGAGCGCC | AGCGAGGTGG | ACCGGATGTT | 1980 |
| CCCCGGGGTG | CCTTTGGACA | CGCACGACGT | CTTCCAGTAC | CGAGAGAAAG | CCTATTTCTG | 2040 |
| CCAGGACCGC | TTCTACTGGC | GCGTGAGTTC | CCGGAGTGAG | TTGAACCAGG | TGGACCAAGT | 2100 |
| GGGCTACGTG | ACCTATGACA | TCCTGCAGTG | CCCTGAGGAC | TAGGGCTCCC | GTCCTGCTTT | 2160 |
| GCAGTGCCAT | GTAAATCCCC | ACTGGGACCA | ACCCTGGGGA | AGGAGCCAGT | TTGCCGGATA | 2220 |
| CAAACTGGTA | TTCTGTTCTG | GAGGAAAGGG | AGGAGTGGAG | GTGGGCTGGG | CCCTCTCTTC | 2280 |

```
TCACCTTTGT  TTTTGTTGG  AGTGTTTCTA  ATAAACTTGG  ATTCTCTAAC  CTTT                    2 3 3 4
```

( 2 ) INFORMATION FOR SEQ ID NO:34:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:34:

```
Glu  Ala  Leu  Met  Tyr  Pro  Met  Tyr  Arg  Phe  Thr  Glu  Gly  Pro  Pro  Leu
1                   5                        10                       15
His  Lys
```